United States Patent [19]
Goodbody et al.

[11] Patent Number: 5,569,745
[45] Date of Patent: Oct. 29, 1996

[54] PEPTIDE-CHELATOR CONJUGATES

[75] Inventors: Anne Goodbody; Alfred Pollak, both of Toronto, Canada

[73] Assignee: Resolution Pharmaceuticals Inc., Mississauga, Canada

[21] Appl. No.: 202,178

[22] Filed: Feb. 25, 1994

[51] Int. Cl.$^6$ .............. A61K 38/00; C07K 5/00; C07K 7/00
[52] U.S. Cl. .......... 530/328; 530/329; 530/330
[58] Field of Search ................. 530/330, 329, 530/328

[56] References Cited

U.S. PATENT DOCUMENTS

| | | | |
|---|---|---|---|
| 5,433,816 | 8/1995 | Zamora et al. | 424/1.69 |
| 5,480,970 | 1/1996 | Pollak et al. | 530/328 |

FOREIGN PATENT DOCUMENTS

| | | | |
|---|---|---|---|
| 9317719 | 9/1993 | WIPO | A61K 49/02 |
| WO93/25244 | 12/1993 | WIPO | |
| WO95/13832 | 5/1995 | WIPO | |

OTHER PUBLICATIONS

Beherucci et al., Agents Actions, Special Conf. Issue (1992) C115–C117.

Siemion et al., Int. J. Peptide Prot. Res. 35 (1990) pp. 428–433.

Bump et al., "Isolation And Subunit Composition Of Tuftsin Receptor", Proc. Natl. Acad. Sci., U.S.A., 1986, vol. 83, No. 19, pp. 7187–7191.

Najjar et al., "The Chemistry And Biology of Tuftsin[1]", Lymphokin Reportsd, vol., pp. 157–179.

Konopinska et al., "Elongated Tuftsin Analogues–Synthesis And Biological Investigation", pp. 35–43, vol. 419 Database Cancerlit, Abstract No. 384993.

Florentin et al., "Immunopharmacological Properties Of Tuftsin And Of Some Analogues", pp. 177–191, Database Embase, Elsevier Science Publishers, Abstract No. 5599439.

*Primary Examiner*—Michael P. Woodward
*Assistant Examiner*—Benet Prickril
*Attorney, Agent, or Firm*—Foley & Lardner

[57] ABSTRACT

Peptide-chelator conjugates are provided that when labelled with a traceable metal are useful for diagnostic imaging of sites of inflammation. The peptide component is an antagonist of the naturally occurring tetrapeptide tuftsin while the chelator component serves as a labelling site for metals, in particular radionuclide metals such as technetium-99m.

8 Claims, No Drawings

PEPTIDE-CHELATOR CONJUGATES

FIELD OF THE INVENTION

This invention is in the field of diagnostic imaging, and relates to a peptide targetting agent useful for targetting sites of inflammation.

BACKGROUND OF THE INVENTION

The art of diagnostic imaging exploits targetting agents that in binding or localizing sites selectively within the body, help to resolve the image of diagnostic interest. Monoclonal antibodies for example have been developed to have high affinity and specificity for particular cancer cells and therefore are useful for imaging tumours. Despite high affinity and specificity, antibodies do not provide ideal imaging agents since they are costly to produce on a commercial scale as well as their poor labelling characteristics. In particular, metal labels tend to bind at numerous low-affinity binding sites on antibodies and are released in vivo resulting in undesirable accumulation of the label at non-target sites. An alternative targetting agent to antibodies are small receptor binding peptides. Peptides offer the advantage of efficient labelling facilitated by conjugation to various chelating molecules. Other advantages of peptides over antibodies is their ease of synthesis, rapid tissue penetration and rapid clearance from the body.

A naturally occurring tetrapeptide, tuftsin TKPR (Seq. ID no: 1), was discovered to stimulate phagocytosis by binding to receptors expressed on the outer surface of neutrophils and macrophages. Phagocytosis constitutes a major line of defense for a host against bacterial infections, therefore as a stimulator of phagocytosis tuftsin would be expected to be a good peptide for imaging sites of infectious inflammation. However, studies show that tuftsin labelled with a radionuclide metal undesirably accumulates in non-target tissue. In particular, labelled tuftsin accumulated in the gastrointestinal tract which limits its usefulness as an imaging agent.

In light of the difficulties associated with antibodies, it would be desirable to provide a peptidic targetting agent capable of localizing at sites of inflammation while not having substantial accumulation in non-target tissue.

SUMMARY OF THE INVENTION

Peptide-chelator conjugates are provided that when labelled with a traceable metal are useful for diagnostic imaging of sites of inflammation. The peptide component is an antagonist of the naturally occurring tetrapeptide tuftsin while the chelator component serves as a labelling site for metals, in particular radionuclide metals such as technetium-99m. According to an aspect of the invention, there are provided peptidechelator conjugates in which Thr-Lys-Pro-Pro-Arg (Seq ID no: 2) is coupled at its N-terminus to a metal chelator.

In a particular embodiment of the present invention, the metal chelator component of 15 the conjugate is of the formula I:

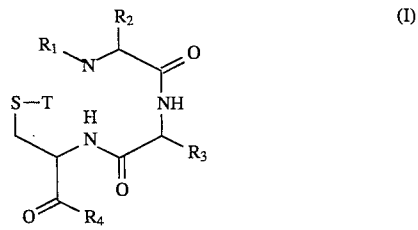

wherein $R_1$ and $R_2$ together form a 5- or 6-membered heterocyclic ring which is optionally fused to a 5- or 6-membered ring wherein either ring is optionally substituted with groups selected from alkyl, alkoxy, carboxyl, halogen, hydroxyl and a linking group;

$R_3$ is selected from H; alkyl; and alkyl substituted by a group selected from amino, aminoacyl, carboxyl, guanidinyl, hydroxyl, thiol, phenyl, phenolyl, indolyl and imidazolyl;

$R_4$ is selected from hydroxyl, alkoxy, and a linking group; and

T represents H or a sulfur protecting group.

In a particular embodiment of the present invention, the metal chelator component of the conjugate is of the formula II:

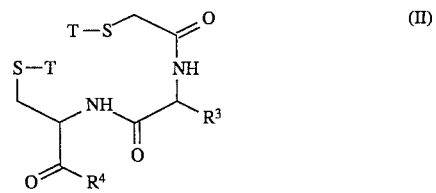

wherein $R_3$, $R_4$ and T are as defined above; and

According to an aspect of the invention, the peptide-chelator conjugates are provided in combination with a diagnostically useful metal or an oxide or nitride thereof.

According to an aspect of the present invention, there is provided a method of imaging a site of inflammation in a mammal, comprising the step of administering a diagnostically effective amount of a composition comprising a peptide-chelator conjugate in which a peptide of the formula Thr-Lys-Pro-Pro-Arg (Seq ID no: 2) is coupled at its N-terminus to a metal chelator which is complexed to a diagnostically useful metal or an oxide or nitride thereof.

DETAILED DESCRIPTION OF THE INVENTION

The invention provides peptide-chelator conjugates that when complexed with a diagnostically useful metal are useful for imaging sites of inflammation. The peptide-chelator conjugate, also referred to as "conjugate", incorporates an antagonist of tuftsin coupled at its N-terminus to any metal chelator, the peptide component consisting of the amino acid sequence Thr-Lys-Pro-Pro-Arg represented by the single letter coed TKPPR (Seq ID no: 2) hereinafter referred to as "the peptide". It is understood that the peptide may be extended at its C-terminus by 1 to 3 amino acid residues or may be modified at the C-terminus for example amidated such that the targetting activity of the peptide is not substantially inhibited. In an embodiment of the present invention, the peptide is coupled to the metal chelators (I) illustrated above which is disclosed in co-pending United States application in the name of Pollak et al, filed on 22 December 1993, incorporated herein by reference and metal chelators (II).

The terms defining the variables $R_1$–$R_4$ and T as used hereinabove in formula (I) and (II) have the following meanings:

"alkyl" refers to a straight or branched $C_1$–$C_8$ chain and includes lower $C_1$–$C_4$ alkyl;

"alkoxy" refers to straight or branched $C_1$–$C_8$ alkoxy and includes lower $C_1$–$C_4$ alkoxy;

"thiol" refers to a sulfhydryl group that may be substituted with an alkyl group to form a thioether;

"sulfur protecting group" refers to a chemical group that is bonded to a sulfur atom and inhibits oxidation of sulfur and includes groups that are cleaved upon chelation of the metal. Suitable sulfur protecting groups include known alkyl, aryl, acyl, alkanoyl, aryloyl, mercaptoacyl and organothio groups.

"linking group" refers to a chemical group that serves to couple the peptide to the chelator while not adversely affecting either the targetting function of the peptide or the metal binding function of the chelator. Suitable linking groups include alkyl chains and amino acid chains functionalized with a reactive groups for coupling to the peptide or chelator.

"metal chelator" refers to a molecule that forms a stable complex with a traceable metal atom under physiological conditions in that the metal remains bound to the conjugate in vivo.

In preferred embodiments of the invention, the chelators conform to the above formulae (I) and (II) in which: $R_1$ and $R_2$ together form a six-membered heterocyclic ring; $R_3$ is selected from H and a hydroxyl substituted alkyl group selected from methyl and ethyl and most preferably hydroxymethyl; $R_4$ is a linking group of one to three amino acid residues and T is the sulfur protecting group acetamidomethyl (Acm) or benzoyl (Bz);

In more preferred embodiments of the invention, the chelators conform to the above formula (I) wherein $R_1$ and $R_2$ together form a pyridine ring; $R_3$ is hydroxymethyl; T is Acm and $R_4$ is a linking group selected from -Gly- and -Gly-Asp-Gly- (Seq ID no: 3). These chelators in a form coupled to the peptide may be represented by the sequences:

Pic-Ser-Cys(Acm)-Gly-TKPPR        (Seq ID no: 4)

and

Pic-Ser-Cys(Acm)-Gly-Asp-Gly-TKPPR        (Seq ID no: 5)

wherein Pic represents the amino acid derivative picolinic acid.

In a preferred embodiment of the invention, the chelators conform to the above formula (II) wherein $R_3$ is hydroxymethyl; T is Acm or Bz and $R_4$ is the linking group -Ser-Gly-Asp-Gly- (Seq ID no: 6). This chelator coupled to the peptide at the linking group of $R_4$ is represented by the sequence:

Bz-MA-Ser-Cys-Ser-Gly-Asp-Gly-TKPPR        (Seq ID no: 7)

wherein Bz-MA represents the group benzoylmercaptoacetic acid.

Peptide-chelator conjugates of the invention may be prepared by various methods depending upon the chelator chosen. The peptide portion of the conjugate is most conveniently prepared by techniques generally established in the art of peptide synthesis, such as the solid-phase approach. Solid-phase synthesis involves the stepwise addition of amino acid residues to a growing peptide chain that is linked to an insoluble support or matrix, such as polystyrene. The C-terminus residue of the peptide is first anchored to a commercially available support with its amino group protected with an N-protecting agent such as a t-butyloxycarbonyl group (tBoc) or a fluorenylmethoxycarbonyl (FMOC) group. The amino protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF).

Peptide and chelator components are coupled to form a conjugate by reacting the free amino group of the Thr residue of the peptide with an appropriate functional group of the chelator such as a carboxyl group or activated ester. For example, a conjugate may incorporate the chelator ethylenediaminetetraacetic acid (EDTA), common in the art of coordination chemistry, when functionalized with a carboxyl substituent on the ethylene chain. Synthesis of EDTA derivatives of this type are reported in Arya et al, (Bioconjugate Chemistry 1991, 2:323) wherein the four coordinating carboxyl groups are each blocked with a t-butyl group while the carboxyl substituent on the ethylene chain is free to react with the amino group of the peptide thereby forming a conjugate.

A conjugate may incorporate a metal chelator component that is peptidic ie. compatible with solid-phase peptide synthesis. In this case the chelator may be coupled to the peptide in the same manner as EDTA described above or more conveniently the chelator and peptide are synthesized in toto starting from the C-terminal residue of the peptide and ending with the N-terminal residue of the chelator.

Conjugates may further incorporate a linking group component that serves to couple the peptide to the chelator while not adversely affecting either the targetting function of the peptide or the metal binding function of the chelator. Suitable linking groups include amino acid chains and alkyl chains functionalized with reactive groups for coupling to both the peptide and the chelator. An amino acid chain is the preferred linking group when the chelator is peptidic so that the conjugate can be synthesized in toto by solid-phase techniques.

An alkyl chain linking group may be incorporated in the conjugate by reacting the amino group of the Thr residue of the peptide with a first functional group on the alkyl chain such as a carboxyl group or an activated ester. Subsequently the chelator is attached to the alkyl chain to complete the formation of the conjugate by reacting a second functional group on the alkyl chain with an appropriate group on the chelator. The second functional group on the alkyl chain is selected from substituents that are reactive with a functional group on the chelator while not being reactive with the Thr residue of the peptide. For example, when the chelator incorporates a functional group such as a carboxyl group or an activated ester, the second functional group of the alkyl chain linking group can be an amino group. It will be appreciated that formation of the conjugate may require protection and deprotection of the functional groups present in order to avoid formation of undesired products. Protection and deprotection is accomplished using protecting groups, reagents and protocols common in the art of organic synthesis. Particularly, protection and deprotection techniques employed in solid phase peptide synthesis described above may be used.

An alternative chemical linking group to an alkyl chain is polyethylene glycol (PEG) which is functionalized in the same manner as the alkyl chain described above for incorporation in the conjugates. It will be appreciated that linking groups may alternatively be coupled first to the chelator and then to the peptide.

In accordance with one aspect of the invention, peptide-chelator conjugates incorporate a diagnostically useful metal capable of forming a complex. Suitable metals include radionuclides such as technetium and rhenium in their various forms such as $^{99m}TcO^{3+}$, $^{99m}TcO_2^+$, $ReO^{3+}$ and $ReO_2^+$. Incorporation of the metal within th conjugate can be achieved by various methods common in the art of coordination chemistry. When the metal is technetium-99m, the following general procedure may be used to form a technetium complex. A peptide-chelator conjugate solution is formed initially by dissolving the conjugate in aqueous alcohol such as ethanol. The solution is then degassed to remove oxygen then thiol protecting groups are removed with a suitable reagent, for example with sodium hydroxide and then neutralized with an organic acid such as acetic acid (pH 6.0–6.5). In the labelling step, a stoichiometric excess of sodium pertechnetate, obtained from a molybdenum generator, is added to a solution of the conjugate with an amount of a reducing agent such as stannous chloride sufficient to reduce technetium and heated. The labelled conjugate may be separated from contaminants $^{99m}TcO_4^-$ and colloidal $^{99m}TcO_2$ chromatographically, for example with a C-18 Sep Pak cartridge.

In an alternative method, labelling can be accomplished by a transchelation reaction. The technetium source is a solution of technetium complexed with labile ligands facilitating ligand exchange with the selected chelator. Suitable ligands for transchelation include tartarate, citrate and heptagluconate. In this instance the preferred reducing reagent is sodium dithionite. It will be appreciated that the conjugate may be labelled using the techniques described above, or alternatively the chelator itself may be labelled and subsequently coupled to the peptide to form the conjugate; a process referred to as the "prelabelled ligand" method.

Another approach for labelling conjugates of the present invention involves techniques described in a co-pending United States application Ser. No. 08/152,680 filed 16 November 1993, incorporated herein by reference. Briefly, the peptide-chelator conjugates are immobilized on a solid-phase support through a linkage that is cleaved upon metal chelation. This is achieved when the chelator is coupled to a functional group of the support by one of the complexing atoms. Preferably, a complexing sulfur atom is coupled to the support which is functionalized with a sulfur protecting group such as maleimide.

When labelled with a diagnostically useful metal, peptide-chelator conjugates of the present invention can be used to detect sites of inflammation by procedures established in the art of diagnostic imaging. A conjugate labelled with a radionuclide metal such as technetium-99m may be administered to a mammal by intravenous injection in a pharmaceutically acceptable solution such as isotonic saline. The amount of labelled conjugate appropriate for administration is dependent upon the distribution profile of the chosen conjugate in the sense that a rapidly cleared conjugate may be administered in higher doses than one that clears less rapidly. Unit doses acceptable for imaging inflammation are in the range of about 5–40 mCi for a 70 kg individual. In vivo distribution and localization is tracked by standard scintigraphic techniques at an appropriate time subsequent to administration; typically between 30 minutes and 180 minutes depending upon the rate of accumulation at the target site with respect to the rate of clearance at non-target tissue.

The following examples are presented to illustrate certain embodiments of the present invention.

EXAMPLE 1
Preparation of Conjugates:

| | |
|---|---|
| Pic—Ser—Cys(Acm)—G—TKPPR | (Seq ID no: 4) |
| Pic—Ser—Cys(Acm)—GDG—TKPPR | (Seq ID no: 5) |
| Bz—MA—Ser—Cys—SGDG—TKPPR | (Seq ID no: 7) |

Peptide-chelator conjugates were synthesized in toto using 9-fluorenylmethyloxycarbonyl (FMOC) chemistry on an 2-methoxy-4-alkoxybenzyl alcohol resin preloaded with the protected C-terminus residue (Sasrin resin, Bachem Biosciences Inc., Philadelphia Pa.) using an Applied Biosystems 433A peptide synthesizer (Foster City, Calif.). N-terminus residues Pic and Bz-MA were incorporated by using picolinic acid and benzoylmercaptoacetic acid respectively as the final residue in the synthesis.

The resin bound conjugate was dried in vacuo for 12 hours. Cleavage of the conjugate from the resin involved mixing a cooled solution of 95% trifluoroacetic acid (TFA) and 5% water (1 ml per 100 mg of peptide-resin) with the conjugate-resin for 1.5 to 2 hours at room temperature. The resin was removed by filtration and washed 3 times with 30 ml t-butyl methyl ether in a 50 ml conical polypropylene centrifuge tube forming a white precipitate. The precipitate was dissolved in water with added acetonitrile. The precipitate was frozen in acetone-dry ice and lyophilized over 12 hours. The resulting white powder was dissolved in water, filtered through a 0.45 μm syringe filter (Gelman Acrodisc LC PVDF) and purified by reversed-phase HPLC (Beckman System Gold) with a $C_{18}$ column (Waters RCM 25×10) using 0.1% TFA in water as buffer A and 0.1% TFA in acetonitrile as buffer B. The column was equilibrated with 100:0 buffer A: buffer B and eluted with a linear gradient in 25 min at 1 ml/min to 50% buffer B. Fractions were reanalysed on the HPLC and pooled according to matching profiles. When necessary the pooled fractions were repurified using the same conditions. The pure fractions were frozen in acetone-dry ice and lyophilized over 10 hours to give a white powder.

EXAMPLE 2

Labelling and Imaging of Conjugates

Imaging studies were performed in a rat inflammation model as follows. Male Wistar rats (Charles River, 150–200g) were injected intramuscularly with a virulent *E. coli* (ATCC 25922, 0.1 ml of 0.5×10⁹ organisms/ml) suspension into their left hindlegs 24 hours before imaging. Focal inflammation in the leg was visually detectable after 1 day.

Each conjugate (50 μl, 2 mg/ml saline) was placed in a 1.5 ml tube with 100 μl saline, 100 μl pertechnetate (10 mCi) and 100 μl stannous gluconate (50 μg stannous chloride and 1 mg sodium gluconate). The tube was capped and placed in a boiling water bath for 10 minutes and then filtered through a Watman PVDF syringe to collect the labelled conjugate solution which was further diluted with saline to prepare an injectable solution (200 μl) containing about 100 μCi (3.7 MBq) of activity. The rats were anaesthetized with somnotol (40 to 50 mg/kg), and the Tc-99m labelled conjugate solution (200 μL) was injected intravenously via the tail vein. Serial whole-body scintigrams were acquired 30 minutes after administration with a gamma camera. The rats were then killed with anaesthesia and samples of organs, urine, blood, inflamed muscle (left leg) and non-inflamed muscle (right leg) were weighed and counted in either a well-type gamma counter or in a gamma dose calibrator. The blood dose calculations were made based on assumptions, (1) that the rat weighed 200 g and (2) that the blood volume constituted 8% of body weight. Results presented in the following table are averages of multiple trials and are corrected for the residual dose in the tail.

| Chelator | Linking Group | Peptide | Time (min) | Urine | G.I. tract | Blood | Inflam muscle | Uninfl muscle | Inflam: Uninfl |
|---|---|---|---|---|---|---|---|---|---|
| Pic—Ser—Cys(Acm)— | —Gly— | —TKPR[e] | 35 | 22.8 | 22.8 | 0.268 | 0.120 | 0.040 | 3.0 |
| Pic—Ser—Cys(Acm)— | —Gly— | —KPPR[b] | 45 | 43.5 | — | 0.220 | 0.125 | 0.059 | 2.1 |
| Pic—Ser—Cys(Acm)— | —Gly— | —TKPRTKPR[c] | 35 | 16.1 | 4.2 | 0.136 | 0.071 | 0.022 | 3.2 |
| Pic—Ser—Cys(Acm)— | Ala—OH \| —G—G—(NH$_\epsilon$—Lys)—Gly—[a] | forTKPPR— | 35 | 12.2 | 11.3 | 0.748 | 0.213 | 0.086 | 2.5 |
| Pic—Ser—Cys(Acm)— | Ala—OH \| —NH—(NH$_\epsilon$—Lys)—Gly— | forTKPPR— | 35 | 14.3 | 9.2 | 0.485 | 0.163 | 0.062 | 2.6 |
| Pic—Ser—Cys(Acm)— | —Gly— | —RTKPR[d] | 35 | 45.4 | 15.0 | 0.169 | 0.099 | 0.033 | 3.0 |
| Bz—MA—Ser—Cys— | —SGDG[g] | —TKPPR[f] | 35 | 47.8 | — | 0.483 | 0.226 | 0.057 | 4.0 |
| Pic—Ser—Cys(Acm)— | —GDG— | —TKPPR[f] | 35 | 63.1 | — | 0.288 | 0.166 | 0.034 | 4.9 |
| Pic—Ser—Cys(Acm)— | —Gly— | —TKPPR[f] | 30 | 44.71 | 5.08 | 0.392 | 0.154 | 0.052 | 3.6 |
| Pic—Ser—Cys(Acm)— | —Gly— | —TKPPR[f] | 180 | 80.62 | 3.71 | 0.048 | 0.026 | 0.006 | 4.7 |

[a] Seq ID no: 8
[b] Seq ID no: 9
[c] Seq ID no: 10
[d] Seq ID no: 11
[e] Seq ID no: 1
[f] Seq ID no: 2
[g] Seq ID no: 6

Results provided in the table reveal that conjugates in which the TKPPR (SEQ ID No: 2) peptide is coupled N-terminally to a chelator exhibited significantly higher ratios of inflamed to uninflamed muscle readings (target to background) as well as superior distribution profiles compared to conjugates incorporating other peptides. Because of these superior properties, the TKPPR (SEQ ID No: 2)-containing conjugates gave images that most clearly differentiated the inflamed muscle tissue. These desirable imaging results were obtained regardless of whether the TKPPR peptide (SEQ ID No: 2) was coupled to an $N_2S_2$ or an $N_3S$ class chelator; both exhibited high target to background and rapid clearance into the urine. The presence and nature of the linking group also did not adversely affect the imaging results with TKPPR (SEQ ID No: 2); conjugates incorporating different linking groups, varying from 1 to 4 amino acids long, also yielded good images.

On the other hand, conjugates containing a metal chelator coupled to the native tuftsin peptide or to peptides structurally related to TKPPR (SEQ ID No: 2) showed target to background ratios significantly lower than the TKPPR (SEQ ID No: 2) conjugates, and showed high accumulation in the GI tract. The one exception, the TKPRTKPR (SEQ ID No: 10) (tuftsin dimer) conjugate, did exhibit low accumulation in the GI tract and blood, nevertheless the particularly low urine levels suggest undesired accumulation at an unknown location. When coupled to the chelator at its C-terminus, the peptide TKPPR (Seq ID no: 2) also exhibited the less desirable properties of relatively low target to background and high GI tract accumulation, resulting in a less resolved image.

The results indicate that conjugates incorporating the peptide TKPPR (Seq ID no: 2), coupled to a chelator at its N-terminus, are useful for imaging inflammation and that this indication is independent of the type of chelator or linking group incorporated in the conjugate.

We claim:

1. A peptide-metal chelator conjugate useful for imaging of sites of inflammation, wherein said metal chelator is coupled to the N-terminus of a peptide consisting of the sequence Thr-Lys-Pro-Pro-Arg (SEQ ID No: 2), wherein the metal chelator has the general formula:

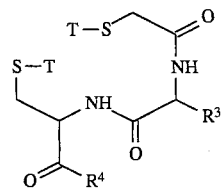

wherein $R_3$ is selected from H; alkyl; and alkyl substituted by a group selected from amine, aminoacyl, carboxyl, guanidinyl, hydroxyl, thiol, phenyl, phenolyl, indolyl and imidazolyl;

$R_4$ is selected from hydroxyl, alkoxy and a linking group; and T represents H or a sulfur protecting group.

2. A peptide-metal chelator conjugate according to claim 1, wherein the peptide is coupled to the metal chelator at $R_4$.

3. A peptide-metal chelator conjugate according to claim 1, wherein the peptide is coupled to the metal chelator by a linking group at $R_4$.

4. A peptide-metal chelator conjugate according to claim 3, wherein the linking group is one or more amino acid residues.

5. A peptide-metal chelator conjugate according to claim 3, wherein the linking group is selected from -Gly-, -Gly-Asp-Gly- (SEQ ID No: 3) and -Ser-Gly-Asp-Gly- (SEQ ID No: 6).

6. A peptide-metal chelator conjugate complex, wherein said peptide-metal chelator conjugate is useful for imaging of sites of inflammation, and wherein said metal chelator is coupled to the N-terminus of a peptide consisting of the sequence THr-Lys-Pro-Pro-Arg (SEQ ID NO: 2), and wherein the metal chelator has the metal chelator has the general formula:

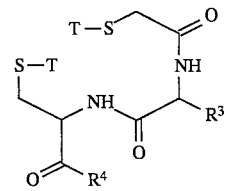

wherein $R_3$ is selected from H; alkyl; and alkyl substituted by a group selected from amino, aminoacyl, carboxyl, guanidinyl, hydroxyl, thiol, phenyl, phenolyl, indolyl and imidazolyl;

$R_4$ is selected from hydroxyl, alkoxy and a linking group; and T represents H or a sulfur protecting group; and a diagnostically useful metal or an oxide or nitride thereof.

7. A peptide-metal chelator conjugate useful for imaging of sites of inflammation, having the formula:

Bz-MA-Ser-Cys-SGDG-TKPPR (SEQ ID NO: 2).

8. A peptide-chelator conjugate according to claim 7, in a form complexed with a diagnostically useful metal or an oxide or nitride thereof.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Thr Lys Pro Arg
1
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Thr Lys Pro Pro Arg
1               5
```

( 2 ) INFORMATION FOR SEQ ID NO:3:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly Asp Gly
1
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Ser substituted with
            picolinic acid (Pic)."

( i x ) FEATURE:
        ( A ) NAME/KEY: Modified-site
        ( B ) LOCATION: 2
        ( D ) OTHER INFORMATION: /note="Cys substituted with
            acetamidomethyl (Acm)."

( x i ) SEQUENCE DESCRIPTION: SEQ ID NO:4:

```
Ser Cys Gly Thr Lys Pro Pro Arg
1               5
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Ser substituted with
            picolinic acid (Pic)."

( i x ) FEATURE:
        ( A ) NAME/KEY: Modified-site
        ( B ) LOCATION: 2
        ( D ) OTHER INFORMATION: /note="Cys substituted with acetamidomethyl (Acm)."

( x i ) SEQUENCE DESCRIPTION: SEQ ID NO:5:

Ser Cys Gly Asp Gly Thr Lys Pro Pro Arg
1               5                       10

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Ser Gly Asp Gly
1

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Ser is substituted with
            benzoylmercaptoacetic acid (Bz-MA)."

( i x ) FEATURE:
        ( A ) NAME/KEY: Modified-site
        ( B ) LOCATION: 2
        ( D ) OTHER INFORMATION: /note="Cys is substituted with
            acetamidomethyl (Acm)."

( x i ) SEQUENCE DESCRIPTION: SEQ ID NO:7:

Ser Cys Ser Gly Asp Gly Thr Lys Pro Pro Arg
1               5                       10

( 2 ) INFORMATION FOR SEQ ID NO:8:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note="Lys is optionally
            substituted at its epsilon amino group with
            Gly-Gly-."

( x i ) SEQUENCE DESCRIPTION: SEQ ID NO:8:

Gly Lys Ala
1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Lys Pro Pro Arg
1

( 2 ) INFORMATION FOR SEQ ID NO:10:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Thr Lys Pro Arg Thr Lys Pro Arg
1                5

( 2 ) INFORMATION FOR SEQ ID NO:11:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Arg Thr Lys Pro Arg
1            5